United States Patent
Zou et al.

(10) Patent No.: US 10,519,081 B1
(45) Date of Patent: Dec. 31, 2019

(54) PROCESS FOR THE PREPARATION OF A BICYCLIC FUSED-RING ALKANE

(71) Applicant: Tianjin University, Tianjin (CN)

(72) Inventors: Jijun Zou, Tianjin (CN); Genkuo Nie, Tianjin (CN); Lun Pan, Tianjin (CN); Xiangwen Zhang, Tianjin (CN)

(73) Assignee: TIANJIN UNIVERSITY, Tianjin (CN)

( * ) Notice: Subject to any disclaimer, the term of this patent is extended or adjusted under 35 U.S.C. 154(b) by 0 days.

(21) Appl. No.: 16/158,326

(22) Filed: Oct. 12, 2018

(30) Foreign Application Priority Data

Jul. 24, 2018 (CN) .......................... 2018 1 0821200

(51) Int. Cl.
| | | |
|---|---|---|
| *C07C 1/20* | (2006.01) | |
| *C07C 13/47* | (2006.01) | |
| *C07C 5/02* | (2006.01) | |
| *C07C 13/50* | (2006.01) | |
| *C07C 5/25* | (2006.01) | |

(52) U.S. Cl.
CPC ................ *C07C 13/50* (2013.01); *C07C 5/02* (2013.01); *C07C 5/2518* (2013.01); *C07C 2529/40* (2013.01); *C07C 2529/85* (2013.01); *C07C 2529/89* (2013.01); *C07C 2602/28* (2017.05)

(58) Field of Classification Search
None
See application file for complete search history.

(56) References Cited

FOREIGN PATENT DOCUMENTS

CN      107628920 A      1/2018

OTHER PUBLICATIONS

Cyclitol, The Free Dictionary, p. 1-2, (2019) (Year: 2019).*
Sheng et al., Synthesis of high density aviation fuel with cyclopentanol derived from lignocellulose, Scientific Reports, 5, 9565, p. 1-4, (2015). (Year: 2015).*
Nie et al., One-pot production of branched decalins as high-density jet fuel from monocyclic alkanes and alcohols, Chemical Engineering Science, 180, p. 64-69, (2018). (Year: 2018).*
Tao Zhang et al., "Synthesis of High-Density Aviation Fuel with Cyclopentanol", ACS Sustainable Chem. Eng. 2016, 4, 6160-6166.

* cited by examiner

*Primary Examiner* — Philip Y Louie
(74) *Attorney, Agent, or Firm* — Gokalp Bayramoglu

(57) ABSTRACT

A process for preparation of a bicyclic fused-ring alkane. In the presence of a bifunctional solid catalyst, one or more cyclitols undergo a C—C coupling reaction with itself or each other at a temperature and in a nitrogen gas atmosphere, to produce a bicyclic alkane precursor mixture; then, the nitrogen gas is replaced by hydrogen gas, and the bicyclic alkane precursor mixture is hydrogenated or hydrodeoxygenated at a temperature and under a pressure, to produce the bicyclic fused-ring alkane. The proportion of the bicyclic fused-ring alkane in the product as prepared according to the process is not lower than 80 wt %.

3 Claims, 1 Drawing Sheet

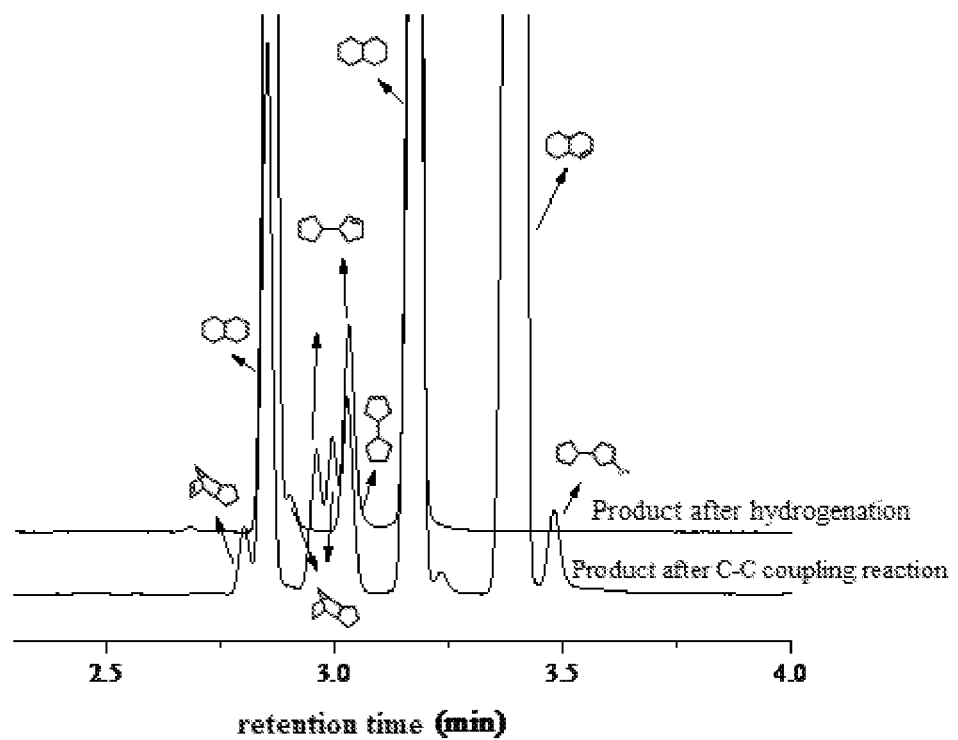

PROCESS FOR THE PREPARATION OF A BICYCLIC FUSED-RING ALKANE

CROSS REFERENCE TO RELATED APPLICATIONS

This application is based upon and claims priority to Chinese Patent Application No. 201810821200.1, filed on Jul. 24, 2018, the entire contents of which are incorporated herein by reference.

TECHNICAL FIELD

The invention is in the field of organic fuels, and particularly it relates to a process for the preparation of a bicyclic fused-ring alkane having controllable compositional ratios.

BACKGROUND

High-density hydrocarbon fuels, as important components of jet fuels, are one of factors capable of deciding the performances of spacecraft, and the fuels may be monocomponent hydrocarbon compound or mixtures comprising a plurality of hydrocarbon compounds. The fuels can be used in engines of turbojets, ramjets and rockets. Developments in the aerospace engineering have put forward high requirements on this kind of high-density fuels: on one hand, the high-density fuels are required to provide more propulsion kinetic energy under the circumstance that the volumes of fuel tanks are given, i.e., the fuels have higher density and higher volume caloric values; on the other hand, the high-density fuels are further required to have good low temperature flow ability.

Naphthalene-derived alkanes have a bicyclic fused-ring structure that is very stable, and thus they can be used as stabilizers in fuels, to inhibit thermal decomposition of the fuels. Naphthalene-derived alkanes are commonly prepared from coal-based compounds. Decalin is one of the naphthalene-derived alkanes, having a density of 0.88 g/mL, an ice point less than −30° C., and a net combustion caloric value higher than 37.4 MJ/L, and thus it, due to the good stability to heat and oxygen, is a predominant component of high-density jet fuels, for example, JP-900. Alkyl-substituted naphthalene-derived alkanes have good low-temperature flow ability and high thermal stability, while keeping high density.

Bicyclic fused-ring alkanes (e.g., naphthalene-derived alkanes) in the art are usually prepared by a two-step process or by a multi-step process. In the first step, selected raw materials, such as cycloalkenes or cyclitols, are used to synthesize unsaturated bicyclic compounds or oxygen-containing bicyclic compounds by the C—C coupling reaction. The corresponding product, after being purified by separations, undergoes the reaction in the second step, that is, under severe conditions, the unsaturated bicyclic compounds or the oxygen-containing bicyclic compounds undergo hydrogenation or deoxygenation to produce bicyclic fused-ring alkanes (such as naphthalene-derived alkanes). The prior art process involves the following defects:

1. The reaction operations are complex, and the yield of the corresponding product is low. For example, Zhang et al. (see ACS Sustainable Chem. Eng., 2016, 4 (11), 6160-6166) prepares the decalin with cyclopentanol as the raw material according to the following steps: the cyclopentanol is first catalytically dehydrated to produce cyclopentene that is purified by separation; then, the cyclopentene is catalytically alkylated to produce a precursor of decalin and other fuels, the precursor being purified by separation; at last, the precursor is hydrogenated under high pressure to produce decalin; the yield of the target product decalin is only 55.3%.

2. A C—C coupling reaction will produce a bicyclic fused-ring product and a linear bicyclic product, and accordingly, the final product obtainable after the hydrogenation also includes a bicyclic fused-ring alkane and a linear bicyclic alkane, wherein the bicyclic fused-ring alkane is the desirable target product. However, the molar ratio of the target product to the linear bicyclic alkane cannot be effectively controlled. Said bicyclic fused-ring product is meant to that the two rings share the same one C—C bond on a ring; said linear bicyclic product is meant to that the two rings are connected by one C—C bond that is not on a ring.

3. The hydrogenation reaction will highly require the catalyst and the associated apparatus used therein. For example, hydrogenating a unsaturated bicyclic compound, such as naphthalene, shall undergo a two-stage high-pressure hydrogenation process: in the first stage, the naphthalene is intermediately hydrogenated to produce tetralin, and a majority of sulfur present in the raw material is removed; in the second stage, the tetralin is deeply hydrogenated to produce decalin; in the process, the deep hydrogenation step of the tetralin is severe, and the temperature as required by the hydrogenation stage is high. In the hydrogenation steps, commonly-used catalysts include nickel catalysts, platinum-molybdenum catalysts, platinum-aluminum catalysts and nickel-aluminum catalysts; while the hydrogen gas pressure in the reaction is different according to different catalysts and reaction conditions as used therein, the pressure as required by the reaction is generally high, usually higher than 6 MPa, and even up to 20 MPa. In general, when the hydrogen gas pressure is lower than 6 MPa, the full hydrogenation will be hardly accomplished.

In the prior art, there are some processes for preparation of naphthalene-derived alkanes by hydrogenating naphthalene or naphthalene substitutes. However, the raw materials for these processes are naphthalene or naphthalene substitutes which are primarily derived from coal tar, a byproduct of coking, and from petroleum distillations, and they have few sources, which limits the scale industrial production of the naphthalene-derived alkanes. In addition, the aforementioned defects in the item 3 are still involved.

The Chinese patent with the application number 2017107835706 discloses a method for the preparation of an alkyl-substituted naphthalene-derived alkane. However, the method involves the following defects: a. catalysts used therein are required to have anacidity-$H_0$ of greater than 12.3, and a working temperature of at most 120° C.; b. in the reaction, coking is severe, which results in rapid decrease of the activity of the catalyst; c. the yield of the product naphthalene-derived alkanes is low, generally 75% or below.

In order to overcome the aforementioned defects, the invention is proposed.

SUMMARY

In order to address the problem that processes for preparation of bicyclic fused-ring alkanes in the art have the defects in complex step, severe reaction conditions and limited source of raw material, the invention is provided with a process for the preparation of a bicyclic fused-ring alkane. The bicyclic fused-ring alkanes as prepared according to the process of the invention have a proportion of not lower than 80% in the product, and the resultant product, for use in jet fuels, has the advantages in high density, high volume caloric value, and a low ice point.

The objective of the invention is accomplished by the following technical solution:

A first aspect of the invention discloses a process for the preparation of a bicyclic fused-ring alkane, wherein in the presence of a bifunctional solid catalyst, one or more cyclitols undergo a C—C coupling reaction with itself or each other at a temperature and in a nitrogen gas atmosphere, to produce a bicyclic alkane precursor mixture; then, the nitrogen gas is replaced by hydrogen gas, and the bicyclic alkane precursor mixture is hydrogenated or hydrodeoxygenated at a temperature and under a pressure, to produce said bicyclic fused-ring alkane.

Preferably, said cyclitols are one or more compounds selected from the group consisting of cyclopentanol, methyl cyclopentanol, dimethyl cyclopentanol, ethyl cyclopentanol, propyl cyclopentanol, cyclohexanol, methyl cyclohexanol, dimethyl cyclohexanol, ethyl cyclohexanol, propyl cyclohexanol, cycloheptanol, methyl cycloheptanol, dimethyl cycloheptanol, ethyl cycloheptanol, propyl cycloheptanol or 5-ethyl-3-methyl cycloheptanol.

Preferably, said bifunctional solid catalysts are one or more materials selected from the group consisted of Pd/SAPO, CoMo/HY, Ni/HZSM-5, CuCo/Hβ, Ir/Al-SBA-15, PtNi/Al-SBA-16, Ru/Ti-MCM-41, Pt/H-ZSM-5, PdFe/H-ZSM-5, Au/LaY, Pt/Al-SBA-16 and Pt/Hβ.

Preferably, the acidity —$H_0$ of the bifunctional solid catalyst is not lower than 3.5; the bifunctional solid catalyst is added in an amount from 1 wt % to 20 wt % based on the total weight of the reactants.

Preferably, the acidity —$H_0$ of the bifunctional solid catalyst is in the range from 4.4 to 12.

Preferably, the temperature of the C—C coupling reaction ranges from 100 to 250° C.; the temperature of the hydrogenation or the hydrodeoxygenation is in the range from 90 to 160° C., and the pressure of the hydrogen gas is in the range from 2 to 6 MPa.

The raw material cyclitol as used in the invention and the intermediate bicyclic alkane precursor mixture present in the reaction procedure are shown by the following schemes:

(a): Cyclitol

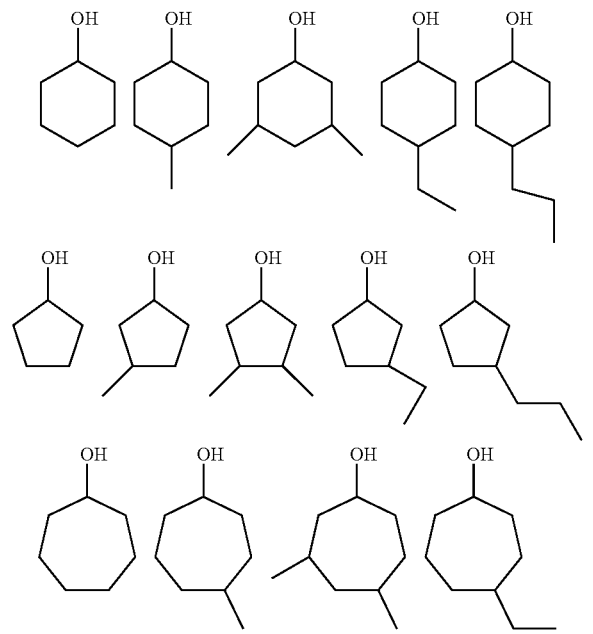

-continued

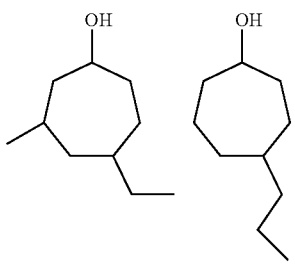

(b): Intermediate bicyclic alkane precursor mixture, comprising a bicyclic fused-ring product and a linear bicyclic product, wherein the bicyclic fused-ring product is shown by the following schemes:

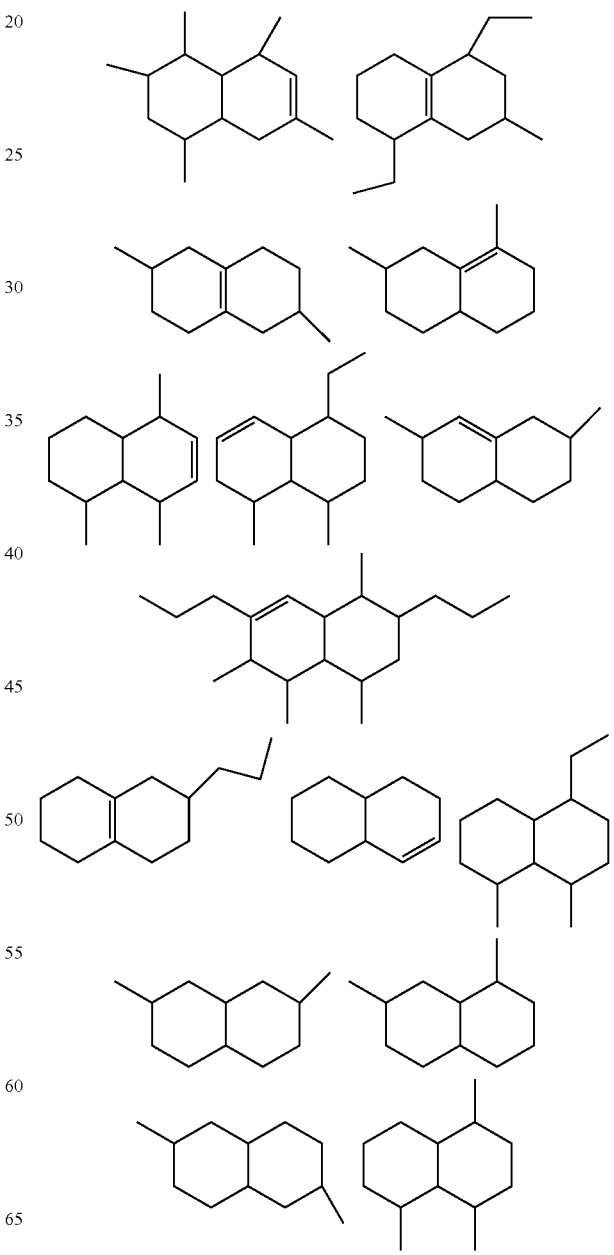

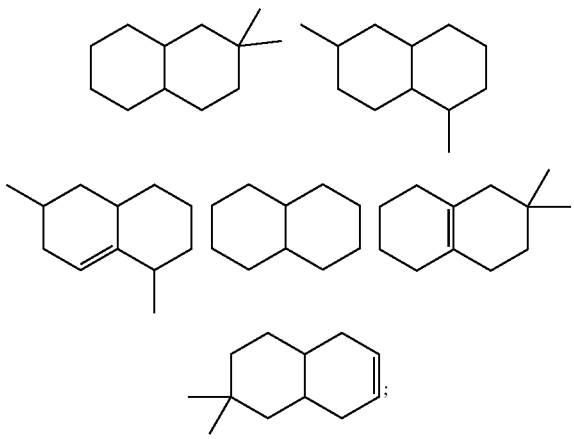
and
Wherein the linear bicyclic product is shown by the following schemes:
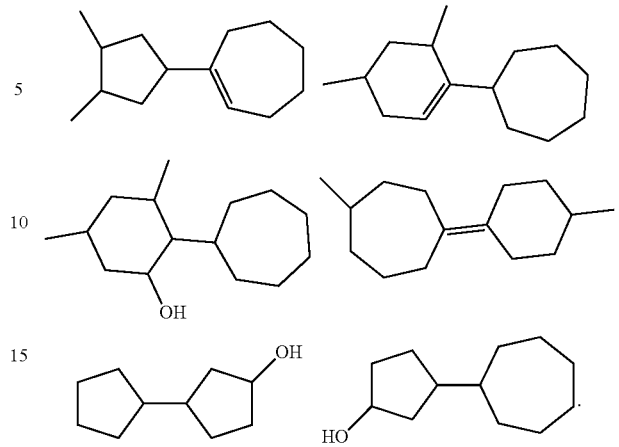
The product as prepared by the process according to the invention also includes a bicyclic fused-ring alkane and a linear bicyclic alkane, wherein some representative schemes of the bicyclic fused-ring alkane are shown as follows:
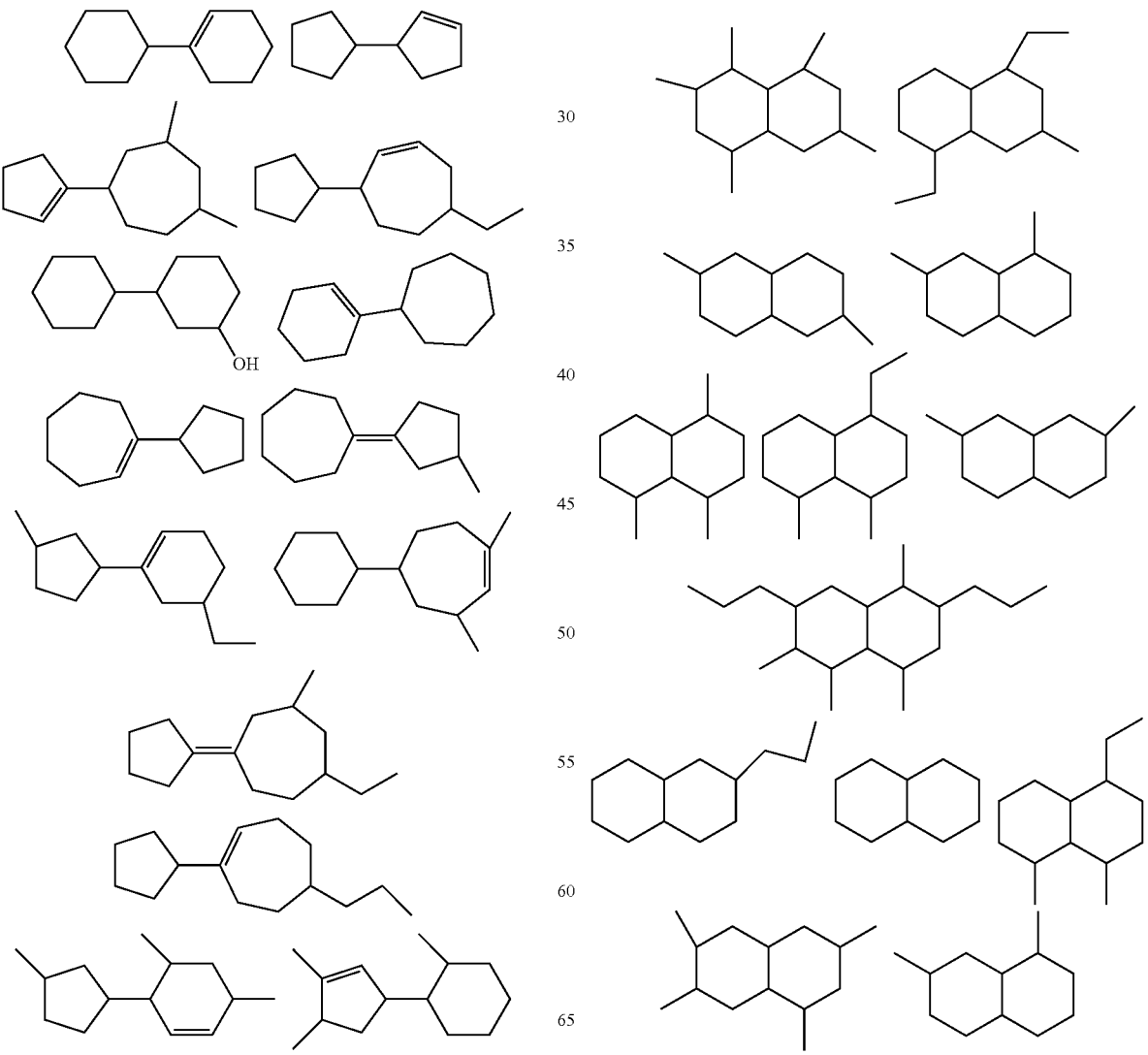

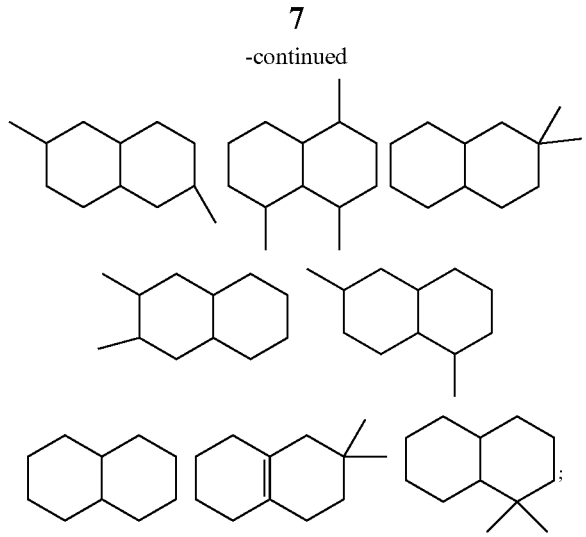
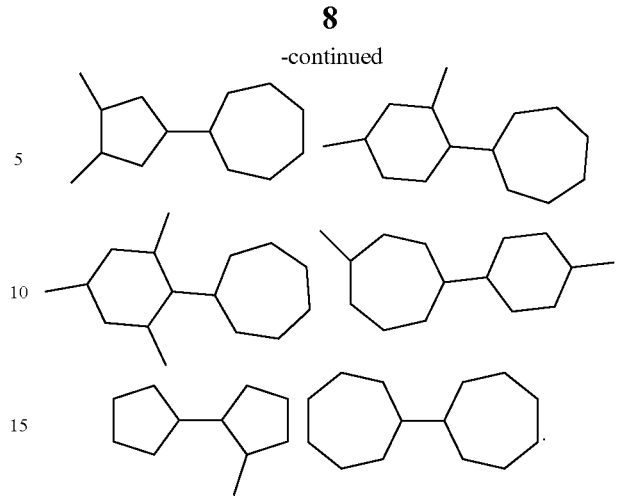

and

Wherein some representative schemes of the linear bicyclic alkane are shown as follows:

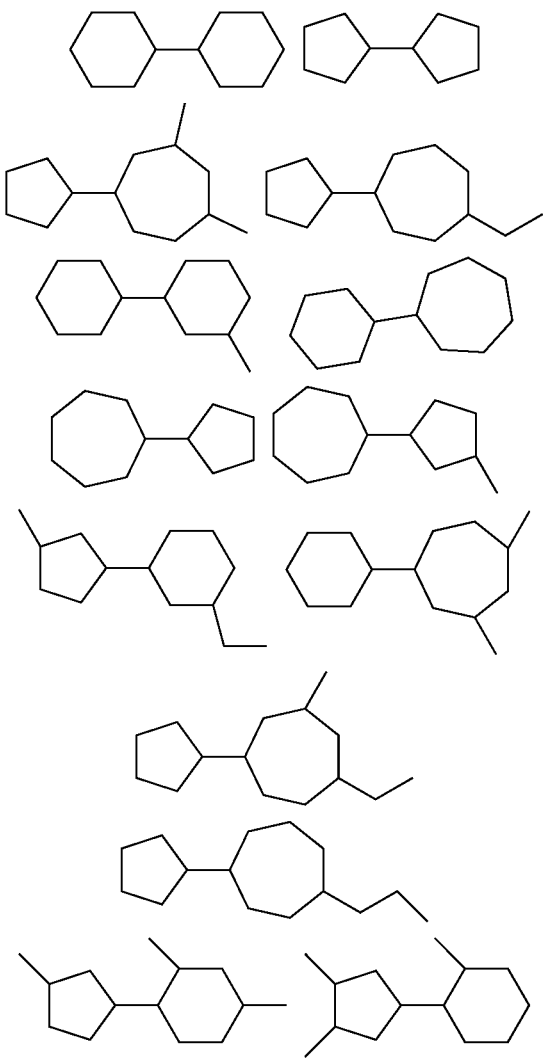

In the invention, percent amounts that are not particularly specified, each are a mass percent amount.

Beneficial Effects of the Invention

1. Directed to the defect in the art that the preparation of fused-ring alkanes requires separations and purifications, the process according to the invention prepares a bicyclic fused-ring alkane product by a one-pot method with two steps in which a supported bifunctional solid catalyst comprising metal sites and acidic sites are used as the catalyst and a cyclitol is used as the raw material, thereby to avoid boring transferring and separation operations of intermediate products.

2. Directed to the defect in the art that the proportion of fused-ring alkanes in corresponding product is low, the process according to the invention is performed by using a bifunctional solid catalyst having an acidity —$H_0$ of not lower than 3.5 as the catalyst and a cyclitol as the raw material while controlling corresponding reaction conditions to control the proportion of the bicyclic fused-ring alkane in the final product is not lower than 80%.

3. Directed to the defect in the art that hydrodeoxygenation conditions in processes for preparation of fused-ring alkanes are severe, the conditions as required by the hydrogenation or hydrodeoxygenation step in the process according to the invention are mild. For example, the hydrogen gas pressure is not highly required, and the pressure that is only in the range from 2 to 6 MPa can satisfy the requirement; due to a low requirement on associated apparatus, costs for production of the fused-ring alkanes are low, and thus corresponding industrial production will be easily accomplished.

4. Directed to the defect in the art that raw materials for preparation of fused-ring alkanes have limited sources, the process of the invention prepares a bicyclic fused-ring alkane by a one-pot method in two steps in which cyclitols are used as the raw material. The cyclitol raw materials may be intermediates in petrochemical industry or biomass derivatives, and the raw materials have wide sources.

5. When the acidity —$H_0$ of the bifunctional solid catalyst in the invention is not lower than 3.5, the invention can be achieved. During the reaction procedure, no significant coking phenomena occurs.

BRIEF DESCRIPTION OF THE DRAWINGS

FIGURE is the GC-MS diagram of the bicyclic alkane precursor and bicyclic alkane product as prepared in Example 1 of the invention from cyclopentanol in the presence of the catalyst Pt/Hβ.

DETAILED DESCRIPTION OF THE EMBODIMENTS

The following examples are provided with the purpose of illustrating the contents of the invention, but not of further limiting the protection scope of the invention.

Example 1

33.25 g cyclopentanol and 1.67 g Pt/Hβ (the —$H_0$ of Pt/Hβ is 4.4) were simultaneously added to a high pressure reactor with mechanical stirring, and under the protection with nitrogen gas, the reaction mixture was kept at the temperature 200° C. for carrying out the reaction for 10 hours. Then, the temperature was decreased to 120° C. At this time, the atmosphere was replaced by hydrogen gas, and the corresponding pressure was kept at 4 MPa to go on the reaction for 5 hours, thereby to provide a product.

As shown by analyzing the materials in the reaction procedure, the conversion of the cyclopentanol in the nitrogen gas atmosphere is 100%, and the yield of the bicyclic alkane precursor mixture is 90%. In the hydrogen gas atmosphere, the bicyclic alkane precursor mixture is fully converted, and the yield of the bicyclic alkane is 98%. Hence, in the whole procedure, the conversion of the cyclopentanol is 100%, and the yield of the bicyclic alkane is 88%, wherein the yield of the fused-ring naphthalene-derived alkane is not lower than 80%. The GC-MS spectra of the bicyclic alkane precursor and bicyclic alkane as produced by hydrogenating the bicyclic alkane precursor mixture in the example is shown in FIGURE.

Examples 2-13

Just as Example 1, Pd/SAPO, CoMo/HY, Ni/HZSM-5, CuCo/Hβ, Ir/Al-SBA-15, PtNi/Al-SBA-16, Ru/Ti-MCM-41, Pt/H-ZSM-5, PdFe/H-ZSM-5, Au/LaY, Pt/Al-SBA-16, and Pt/Hβ (the —$H_0$ of these catalyst is in the range from 4.4 to 1.2) were used as the catalyst, and one or more cyclitols were used as the reactants. The results with regard to the reactant and amount thereof, the catalyst and amount thereof, the reaction temperature, the reaction time, the conversion of the reactant and the yield of the bicyclic alkane are shown in the following table:

| Entyy | Catalysts | Acid strength of Acidic supporters (-H0) | Mass of catalyst (g) | Raw materials | Mass of raw material (g) | Temperature of C-C coupling reaction (° C.) | Time of C-C coupling reaction (h) | Hydrogen gas pressure (MPa) | Time of hydrogenation reaction (h) | Temperature of hydrogenation reaction (° C.) | Yield of bicyclic alkanes (%) Bicyclic fused-ring alkanes | Linear bicyclic alkanes |
|---|---|---|---|---|---|---|---|---|---|---|---|---|
| 2 | Pd/SAPO | 5 | 2.8 | Cyclopentanol | 28 | 240 | 18 | 2 | 5 | 100 | 85 | 5 |
| 3 | CoMo/HY | 4.4 | 2.5 | Cyclohexanol | 32.0 | 250 | 25 | 3 | 3 | 120 | 82 | 8 |
| 4 | Ni/H-ZSM-5 | 7 | 2.7 | 20% Cyclohexanol 80% Cyclopentanol | 35 | 140 | 20 | 5 | 5 | 150 | 84 | 9 |
| 5 | CuCo/Hβ | 5 | 3.7 | Dimethyl cyclopentanol | 33 | 170 | 18 | 6 | 4 | 160 | 83 | 2 |
| 6 | Ir/Al-SBA-15 | 7.7 | 3.2 | Ethyl cyclopentanol | 35 | 140 | 16 | 3 | 5 | 100 | 81 | 8 |
| 7 | PtNi/Al-SBA-16 | 6.5 | 3.4 | Propyl cyclohexanol | 32 | 150 | 20 | 3 | 4 | 150 | 80 | 12 |
| 8 | Ru/Ti-MCM-41 | 7 | 3.8 | Butyl cyclopentanol | 35 | 100 | 5 | 2 | 5 | 140 | 80 | 5 |
| 9 | Pt/H-ZSM-5 | 7.2 | 5.5 | Ethyl cyclohexanol | 38 | 110 | 8 | 2 | 4 | 100 | 83 | 8 |
| 10 | PdFe/H-ZSM-5 | 6.7 | 6 | Dimethyl cycloheptanol | 40 | 180 | 15 | 3 | 2 | 110 | 80 | 7 |
| 11 | Au/LaY | 4.5 | 5 | Cycloheptanol | 40 | 120 | 5 | 2.5 | 5 | 100 | 82 | 5 |
| 12 | Pt/Al-SBA-16 | 6 | 6 | Propyl cycloheptanol | 30 | 150 | 10 | 5 | 5 | 90 | 80 | 15 |
| 13 | Pt/Hβ | 7.7 | 5 | 30% Cyclopentanol 30% Methyl cyclopentanol 40% Propyl cyclopentanol | 25 | 140 | 18 | 3 | 10 | 100 | 85 | 5 |

As seen from Examples 1-13, in the presence of the catalysts Pd/SAPO, CoMo/HY, Ni/HZSM-5, CuCo/Hβ, Ir/Al-SBA-15, PtNi/Al-SBA-16, Ru/Ti-MCM-41, Pt/H-ZSM-5, PdFe/H-ZSM-5, Au/LaY, Pt/Al-SBA-16, and Pt/Hβ, a cyclitol underwent the C—C coupling reaction at a temperature ranging from 100° C. to 250° C. in a nitrogen gas atmosphere; the resultant coupling products were hydrogenated or hydrodeoxygenated by hydrogen from 2 to 6 MPa and at a temperature ranging from 90 to 160° C. The conversion of the raw material can reach 100%, and the yield of the resultant bicyclic fused-ring alkane is not lower than 80%. After the above reaction, the catalyst is tested by thermogravimetric analysis (TGA) to find out that in the above catalyst, almost no coking and coal-aggregating phenomena occurs.

As for the product as prepared in Example 1, the density is measured to be 0.89 g/mL according to GB2540-81 "Petroleum products-Determination of density-Pyknometer method"; the freezing point is measured to be lower than −60° C. as determined according to GB2430-81 "Determination of the Ice Point of Jet Fuel"; the dynamic viscosity is measured to be 2.69 mm²/s (20° C.) according to GB265-88 "Petroleum products-Determination kinematic viscosity and dynamic viscosity"; and the net heat value is measured to be 37.0 MJ/L according to GB/T 384-81 "Determination of caloric value of petroleum products". Obviously, the bicyclic fused-ring alkanes as prepared in the invention are high-density fuels having advantages in high density, high net volume caloric value, and low freezing point.

What is claimed is:

1. A process for preparation of a bicyclic fused-ring alkane, comprising:
    producing a bicyclic alkane precursor mixture by a C—C coupling reaction of one or more compounds with itself or each other at a first temperature and in a nitrogen gas atmosphere in presence of a bifunctional solid catalyst;
    then, replacing nitrogen gas of the nitrogen gas atmosphere by hydrogen gas, and hydrogenating or hydrodeoxygenating the bicyclic alkane precursor mixture at a second temperature and under a pressure, to produce the bicyclic fused-ring alkane, wherein
    the one or more compounds is one or more selected from the group consisting of cyclopentanol, methyl cyclopentanol, dimethyl cyclopentanol, ethyl cyclopentanol, propyl cyclopentanol, cyclohexanol, methyl cyclohexanol, dimethyl cyclohexanol, ethyl cyclohexanol, propyl cyclohexanol, cycloheptanol, methyl cycloheptanol, dimethyl cycloheptanol, ethyl cycloheptanol, propyl cycloheptanol and 5-ethyl-3-methyl cycloheptanol,
    the bifunctional solid catalyst is one or more selected from the group consisting of Pd/SAPO, CoMo/HY, Ni/HZSM-5, CuCo/Hβ, Ir/Al-SBA-15, PtNi/Al-SBA-16, Ru/Ti-MCM-41, Pt/H-ZSM-5, PdFe/H-ZSM-5, Au/LaY, Pt/Al-SBA-16 and Pt/Hβ,
    an acidity —$H_0$ of the bifunctional solid catalyst is not lower than 3.5, and the bifunctional solid catalyst is added in an amount from 1 wt % to 20 wt % based on a total weight of reactants of the one or more compounds, and
    the bicyclic fused-ring alkane is decalin or alkyl substituted decalin.

2. The process according to claim 1, wherein, the acidity —$H_0$ of the bifunctional solid catalyst is in a range from 4.4 to 12.

3. The process according to claim 1, wherein, the first temperature of the C—C coupling reaction ranges from 100° C. to 250° C.; the second temperature is in a range from 90° C. to 160° C., and the pressure of the hydrogen gas is in a range from 2 MPa to 6 MPa.

* * * * *